United States Patent [19]

Shibuya et al.

[11] Patent Number: 5,604,211
[45] Date of Patent: Feb. 18, 1997

[54] SACCHARIDE FOR SUPPLEMENTING ENERGY TO LIVING BODY, AND USES

[75] Inventors: Takashi Shibuya; Hiroto Chaen; Shuzo Sakai; Toshio Miyake, all of Okayama, Japan

[73] Assignee: Kabushiki Kaisha Hayashibara Seibutsu Kagaku Kenkyujo, Okayama, Japan

[21] Appl. No.: 347,222

[22] Filed: Nov. 23, 1994

Related U.S. Application Data

[63] Continuation of Ser. No. 86,456, Jul. 6, 1993, abandoned, which is a continuation of Ser. No. 791,683, Nov. 14, 1991, abandoned.

[30] Foreign Application Priority Data

Sep. 20, 1991 [JP] Japan .................................. 3-268683
Sep. 20, 1991 [JP] Japan .................................. 3-268684

[51] Int. Cl.$^6$ .......................... A61K 31/715; A23G 3/00
[52] U.S. Cl. ...................... 514/53; 426/658; 536/123.12
[58] Field of Search ...................... 514/53; 536/123.13; 426/658

[56] References Cited

U.S. PATENT DOCUMENTS

| | | | |
|---|---|---|---|
| 3,741,776 | 6/1973 | Mitsuhashi et al. | 426/552 |
| 3,973,050 | 8/1976 | Hayashibara et al. | 426/552 |

FOREIGN PATENT DOCUMENTS

| | | | |
|---|---|---|---|
| 47-13699 | 4/1972 | Japan | 426/552 |
| 47-42506 | 10/1972 | Japan | 426/552 |
| 63-216492 | 9/1988 | Japan | 536/18.5 |
| 63-240758 | 10/1988 | Japan | 514/53 |

OTHER PUBLICATIONS

Japanese Patent Appl. No. 307,054/1990, Abstract.
Kobayashi, S. et al, Abstract of Japanese Patent No. 240, 757/88 in *Chem Abs* 110:74133g, 1989.
Siddiqui, I. R. et al., *Chem Abs* 69:1880y, 1968.
*Pharmaceutical Dosage Forms and Drug Delivery Systems*, Eds. Ansel, Popovich & Allen, Publ. by Williams & Wilkins, pp. 81–83 & 286–291. (1995).
Japanese Patent Application No. 307,054/1990, *Abstract of the Disclosure.*

*Primary Examiner*—John Kight
*Assistant Examiner*—Howard C. Lee
*Attorney, Agent, or Firm*—Browdy and Neimark

[57] ABSTRACT

A composition for supplementing energy to a living body containing neotrehalose as effective ingredient. Neotrehalose is a disaccharide, therefore, when used in an energy supplementing composition, provides twice as much energy as does a monosaccharide. Neotrehalose has non-reducing properties, and this renders the composition containing neotrehalose stable for a relatively-long time period.

13 Claims, No Drawings

SACCHARIDE FOR SUPPLEMENTING ENERGY TO LIVING BODY, AND USES

This application is a continuation of application Ser. No. 08/086,456 filed on Jul. 6, 1993 now abandoned, entitled SACCHARIDE FOR SUPPLEMENTING ENERGY TO LIVING BODY, AND USES, which is a continuation of Ser. No. 07/791,683, filed Nov. 14, 1991 now abandoned.

BACKGROUND OF THE INVENTION

1. Field of the Invention

The present invention relates to a saccharide for supplementing energy to a living body (hereinafter designated as a "SACCHARIDE" and its preparation, more particularly, it relates to SACCHARIDE which comprises neotrehalose, as well as to a composition for supplementing energy to a living body (hereinafter designated as a "COMPOSITION") which contains neotrehalose as the effective ingredient.

2. Description of the Prior Art

Glucose and fructose, which exhibit reducing properties, are conventional saccharides. These saccharides are, however, unstable because of their inherent reducing properties, and usually, the instability is increased in the presence of other nutritional substances such as amino acids and vitamins.

Therefore, there has been a great demand for the establishment of a SACCHARIDE selected from the group consisting of non-reducing saccharides with a satisfactory stability, for example, xylitol, sorbitol, maltitol, lactitol, sucrose and trehalose. The monosaccharide alcohols (hydrogenated monosaccharides) such as xylitol and sorbitol have, however, a drawback: They give an acute diarrhea when the dose and administration method are not correctly chosen. As described in Japanese Patent Publication Nos.13,699/72 and 42,506/72, the disaccharide alcohols (hydrogenated disaccharides) such as maltitol and lactitol are not readily metabolized and utilized in vivo. They have been used as a low-caloric sweetener and thus are not suitable for use as a SACCHARIDE. Sucrose has a drawback: It is readily hydrolyzed under acidic conditions into glucose and fructose which exhibit reducing properties, and this hinders the storage stability. As Japanese Patent Laid-Open No.240,758/88 describes "Trehalose is a low-caloric sweetener which is not readily metabolized and absorbed by the human body." and "Trehalose is not readily hydrolyzed by enzymes such as amylases.", it has been recognized that trehalose is a saccharide which does not release energy in a living body, and that preparing trehalose in commercial quantities is very difficult and the preparation thereof has not been studied in detail.

SUMMARY OF THE INVENTION

There has been a great demand for a commercially available SACCHARIDE which is free of reducing properties, which has satisfactory storage stability, and which can be used in a variety of fields, as well as for a commercially available SACCHARIDE which contains neotrehalose as an effective ingredient.

The present inventors have studied SACCHARIDEs. In particular, the present inventors studied non-reducing disaccharides such as trehalose and its related substances.

As a result, the present inventors found that unexpectedly, unlike trehalose ($\alpha,\alpha$-trehalose) and isotrehalose ($\beta,\beta$-trehalose), neotrehalose (O-$\alpha$-D-glucopyranosyl $\beta$-D-glucopyranoside or $\alpha,\beta$-trehalose) was readily metabolized and converted by a living body into energy, and that neotrehalose was a SACCHARIDE which can be used in a variety of fields because of its stability and non-reducing properties. The present inventors produced a COMPOSITION which contains neotrehalose as the effective ingredient. Thus, the present inventors accomplished the present invention. Since neotrehalose has a relatively-high storage stability and does not have reducing properties, the present COMPOSITION can be advantageously prepared into a synthetic nutritional composition and a pharmaceutical composition with a higher therapeutic-effect by combining the present COMPOSITION with other nutritional- and/or pharmaceutical-substances.

DETAILED DESCRIPTION OF THE INVENTION

The present invention is the first to provide a SACCHARIDE which comprises neotrehalose, as well as to provide a COMPOSITION which contains neotrehalose as the effective component.

Any method of preparation of the present SACCHARIDE can be used in the invention, as long as it produces the present SACCHARIDE. Neotrehalose which is prepared, for example, either of by the method disclosed in Japanese Patent Laid-Open No.216,492/88, wherein cyclodextrin-synthesizing enzyme is allowed to act on starch or partial starch hydrolysate, and the method, disclosed by the present inventors in Japanese Patent Application No.307,054/90, wherein $\beta$-galactosidase is allowed to act on lactoneotrehalose, can be used in the invention after purification.

Neotrehalose preparations, which have been purified to the possible highest level, are preferably used in the present SACCHARIDE: Usually, neotrehalose preparations in the form of syrup or powder with a neotrehalose content of 50 w/w % or higher, preferably, those in the form of syrup or crystalline powder with a neotrehalose content of 80 w/w % or higher, more preferably, those in the form of crystalline powder or crystal with a neotrehalose content of 90 w/w % or higher are suitably used in the invention.

Any COMPOSITION can be used in the invention, as long as it contains neotrehalose as effective ingredient and can supply energy to a living body, and usually, in order to improve the effect, COMPOSITIONs with a neotrehalose concentration of 10 w/w % or higher, preferably, 20 w/w % or higher on the dry solid basis (abbreviated as "d.s.b." hereinafter) can be favorably used in the invention.

A simple composition consisting of neotrehalose can be used in the invention, and usually, the present COMPOSITION can be prepared by combining neotrehalose with at least one or more of other substances, for example, nutritional substance such as proteins, amino acids, lipids, other saccharides, vitamins and minerals; and pharmaceutically or therapeutically active substances such as antibacterial substances, enzymes, hormones and cytokines. If necessary, at least one or more of other appropriate substances such as flavor-improving agents and coloring agents, flavor-imparting agents, stabilizers, vehicles and fillers, can be used in combination, and the COMPOSITION thus obtained can be formulated to its ultimate use.

The COMPOSITION is orally- and/or parenterally administered without exhibiting toxicity or causing any side effects, and satisfactorily metabolized and utilized in vivo. Thus, the COMPOSITION can be advantageously used to supplement energy to a living body.

The dose of the present SACCHARIDE is chosen from the range of about 1–1,000 g/day/adult, preferably, from the range of about 5–500 g/day/adult based on the weight of neotrehalose, d.s.b., as effective ingredient.

The present SACCHARIDE and COMPOSITION are advantageously administrable to humans, as well as to domestic- and pet-animals such as cows, horses, dogs and cats.

The following Experiments will explain the present invention in detail.

EXPERIMENT 1

Digestion test in vitro

In accordance with the method reported in K. Okada et al., *Journal of Japanese Society of Nutrition and Food Science*, Vol.43, No.1, pp.23–29 (1990), a crystalline neotrehalose specimen formulated by the method in Example A1-2 was prepared as an aqueous solution which was then tested for its digestibility in vitro: The digestibility was determined with the following equation and expressed as hydrolysis rate (%):

$$\text{Hydrolysis rate (\%)} = \frac{\text{Reducing sugar}}{\text{Total sugar}} \times 100$$

The results were as shown in Table 1.

TABLE 1

|  | Hydrolysis rate (%) |
| --- | --- |
| Salivary amylase | 0.0 |
| Gastric juice | 0.0 |
| Amylopsin | 0.0 |
| Enzyme of small intestinal mucous membrane | 43.0 |

As evident from the results in Table 1, neotrehalose is well digested by the enzyme of the small intestinal mucous membrane.

Similarly as above, several kinds of disaccharides were tested for their digestibility using the enzyme of the small intestinal mucous membrane.

The results were as shown in Table 2.

TABLE 2

|  | Hydrolysis rate (%) |
| --- | --- |
| Maltose | 80.1 |
| Sucrose | 25.1 |
| Isomaltose | 13.2 |
| Lactose | 9.7 |
| Cellobiose | 1.2 |
| Trehalose (α,α-trehalose) | 0.4 |
| Neotrehalose (α,β-trehalose) | 43.0 |
| Isotrehalose (β,β-trehalose) | 0.1 |

As evident from the results in Table 2, it was discovered that, unexpectedly, except for maltose, neotrehalose was more digestible than the other disaccharides tested by the enzyme of the small intestinal mucous membrane, and the digestibility of neotrehalose was far higher than that of sucrose.

EXPERIMENT 2

Utilization test in vivo

EXPERIMENT 2-1

In accordance with the method described in H. Atsuji et al., *Journal of Clinical Nutrition*, Vol.41, Vol.2, pp.200–208 (1972), 30 g of a neotrehalose specimen was formulated as a 20 w/v % aqueous solution which was then orally administered to 3 healthy volunteers (26-, 39- and 52-year old men) and their blood was sampled at prescribed time intervals and tested for blood sugar and insulin levels. As a control, glucose was used.

As a result, neotrehalose behaved similarly as glucose, and the maximum values of both blood sugar and insulin levels were observed about 0.5–1 hour after the oral administration.

This confirmed that neotrehalose was readily digested, absorbed, metabolized and utilized to produce energy.

EXPERIMENT 2-2

A neotrehalose specimen prepared by the method in Example A1-2 was treated to remove pyrogens in the usual manner, and 50 g of the resultant neotrehalose specimen was in accordance with the method reported in Matsuzaki, *Yakubutsu Ryoho*, Vol.6, No.2, pp.65–72 (1973), formulated as a 10 w/v % aqueous solution which was then intravenously administered to 2 healthy volunteers (37- and 49-year old men) by instillation. Their blood was sampled at prescribed time intervals and blood sugar and insulin levels were measured, along with the amount of neotrehalose secreted in their urine. As controls, glucose and maltose were used.

As a result, glucose greatly increased the blood sugar and insulin levels, while neotrehalose exhibited the same dynamics as maltose, i.e. neotrehalose slightly increased the blood sugar level but did not greatly increase the insulin level. The amount of glucose in the urine of the volunteers, who had been administered glucose, was less than 10%, while the amount of glucose in the urine of those administered neotrehalose and maltose was less than 20%. These results confirm that neotrehalose is a saccharide which is well metabolized and utilized by a living body, and this renders neotrehalose very useful in SACCHARIDEs and COMPOSITIONs.

EXPERIMENT 3

Acute toxicity

A crystalline neotrehalose specimen, prepared by the method in Example A1-2, was orally administered to 7 week-old dd mice as an acute toxicity test. As a result, no animal death was noted with the administration of up to 5 g of the specimen, and it was difficult to administer a higher dose. Therefore, the toxicity of the tested substance appears to be extremely low.

The present SACCHARIDE which comprises neotrehalose and the present COMPOSITION which contains neotrehalose as effective ingredient are illustrated by the following Examples A and B respectively.

EXAMPLE A1

Neotrehalose

EXAMPLE A1-1

Preparation of lactoneotrehalose

Fifty parts by weight of commercially-available lactose and 50 parts by weight of "PINE-DEX #1", a dextrin product (DE 8) commercialized by Matsutani Chemical Ind., Co., Ltd., Hyogo, Japan, were dissolved in 150 parts by weight of water while heating, and the solution was heated to 60° C., adjusted to pH 6.0, added with 300 units/g dextrin of a cyclomaltodextrin glucanotransferase from *Bacillus stearothermophilus* commercialized by Hayashibara Biochemical Laboratories Inc., Okayama, Japan, allowed to react for 20 hours, and heated at 100° C. for 30 minutes to inactivate the remaining enzyme. Thereafter, the mixture was cooled to 55° C., adjusted to pH 5.0, and 15 units/g dextrin of "Glucozyme", a glucoamylase specimen commercialized by Nagase Biochemicals Ltd., Kyoto, Japan, was added. The mixture was allowed to react for 16 hours, and heated at 100° C. for 15 minutes to inactivate the remaining enzyme. The resultant solution, containing about 24 w/w % lactoneotrehalose, d.s.b., was decolored with activated charcoal, treated with ion exchange ($H^+$- and $OH^-$- form) for deionization and purification, concentrated to give a concentration of about 45 w/w % and subjected to column chromatography, followed by the recovery of lactoneotrehalose-rich fractions. As the fractionating resin was used "Amberlite XT-1016 ($Na^+$-form)", a strongly-acidic cation exchange resin commercialized by Japan Organo Co., Ltd., Tokyo, Japan, which was suspended in water and packed in jacketted-stainless steel columns having an inner diameter of 5.4 cm each. In this case, 4 columns, gel-bed depth of 5 m each, were cascaded to give a total gel-bed depth of about 20 m. While keeping the inner temperature of the columns at 55° C., 5 v/v % of a material saccharide solution was added thereto, and 55° C. water was then passed through the columns at a flow rate of SV 0.3 to effect fractionation. Lactoneotrehalose-rich fractions were obtained. A portion of the lactoneotrehalose-rich fractions, lactoneotrehalose content of about 67 w/w %, d.s.b., which had been pooled through the repetition of the above method, was concentrated to give a concentration of 75 w/w %, and allowed to stand overnight at 20° C. to crystallize. A solution having a high concentration of lactoneotrehalose, which had been prepared by concentrating the lactoneotrehalose-rich fractions to give a concentration of 70 w/w %, was added with the resultant crystal as seed to effect crystallization under gentle-stirring conditions. The resultant massecuite was separated, and the crystal so formed was washed by spraying there onto a small amount of water to obtain a high-purity crystalline lactoneotrehalose which was then dissolved in water and treated similarly as above to effect recrystallization. Thus, about 3 parts by weight of a high-purity crystalline lactoneotrehalose, purity of 99.8 w/w % or higher, was obtained.

EXAMPLE A1-2

Preparation of neotrehalose

One part by weight of a crystalline lactoneotrehalose specimen obtained by the method in Example A1-1 was dissolved in 30 parts by weight of water while heating, and the solution was adjusted to 40° C. and pH 4.5. Ten units/g lactoneotrehalose of "LACTASE-LP", a β-galactosidase specimen commercialized by K.I Chemical Industry, Co., Ltd., Shizuoka, Japan, was added and the mixture was allowed to react for 20 hours. The mixture was then heated at 100° C. for 10 minutes to inactivate the remaining enzyme. Similarly as in Experiment 1, the resultant solution containing about 66 w/w % neotrehalose and about 33 w/w % galactose, d.s.b., was decolored, deionized, purified, concentrated, and subjected to column chromatography using a strongly-acidic cation exchange resin, followed by the recovery of neotrehalose-rich fractions.

A part of the neotrehalose-rich fractions containing about 88 w/w % neotrehalose, d.s.b., was concentrated to give a concentration of 75 w/w %, and allowed to stand overnight at 20° C. to effect crystallization. A solution having a concentration of 70 w/w %, which had been prepared by concentrating the neotrehalose-rich fractions, was added with the resultant crystal as seed to effect crystallization under gentle stirring conditions. The resultant massecuite was separated, and the crystal formed was washed by spraying there onto a small amount of water to obtain a high-purity crystal which was then dissolved in water and recrystallized similarly as above to obtain about 0.15 parts by weight of a high-purity crystalline neotrehalose, purity of 99.8 w/w % or higher.

The product is an orally- and/or parenterally-administrable SACCHARIDE. COMPOSITIONs such as nutritional- and pharmaceutical-compositions can be advantageously prepared by incorporating there onto the product therein.

EXAMPLE A2

Neotrehalose

A solution containing about 66 w/w % neotrehalose, d.s.b., prepared by using the reaction- and purification-methods in Example A1-2, as a material saccharide solution, was concentrated to give a concentration of about 45 w/w %. In order to increase the content of neotrehalose in the resultant solution, which was subjected to column chromatography similarly as the method in Example A1-1 except that "DOWEX 50W×4 ($Ca^{++}$-form)", a strongly-acidic cation exchange resin commercialized by Dow Chemical Company, Midland, Mich., USA, was used as a resin for fractionation to obtain a neotrehalose-rich fraction containing about 85 w/w % neotrehalose, d.s.b. The fraction was concentrated to give a concentration of about 83 w/w %, and the resultant solution was transferred to a crystallizer and admixed with an about one w/w % seed. The mixture was transferred to a tray and allowed to stand at 20° C. for 4 days to effect crystalization and solidification. Thereafter, the resultant solid was pulverized with a cutting-type pulverizer and dried to obtain a crystalline neotrehalose powder containing molasses in the yield of about 70 w/w %, d.s.b.

EXAMPLE B1

Chocolate

Forty parts by weight of cacao paste, 10 parts by weight of cacao butter, and 50 parts by weight of a crystalline neotrehalose specimen obtained by the method in Example A1-2 were mixed, and the mixture was fed to a refiner to reduce the particle size, transferred to a conche, and kneaded therein at 50° C. for 2 days. In the kneading step, 0.5 parts by weight of lecithin was added and dispersed to homogeneity. Thereafter, the temperature of the mixture was adjusted to 31° C. with a thermoregulator, and the mixture was placed into a mold immediately before the solidification of the cacao butter, deaerated with a vibrator, and solidified by passing it through a 10° C. cooling tunnel over a period of 20 minutes. The mixture was removed from the mold and packaged to obtain the captioned product.

The product has an excellent color, gloss and texture, exhibits no hygroscopicity and melts smoothly in the mouth to exhibit a moderate sweetness and smooth flavor. The product can be suitably used as COMPOSITION.

EXAMPLE B2

Chewing gum

Three parts by weight of a gum base was melted by heating until it softened, and admixed with 4 parts by weight of sucrose, 3 parts by weight of a crystalline neotrehalose powder obtained by the method in Example A2, and adequate amounts of a flavoring agent and coloring agent. The mixture was kneaded with a roll in an usual manner, formed and packaged to obtain the captioned product.

The product is a favorable chewing gum having a satisfactory texture and flavor. The product can be advantageously used as a COMPOSITION.

EXAMPLE B3

Custard cream

One hundred parts by weight of corn starch, 30 parts by weight of maltose, 20 parts by weight of sucrose, one part by weight of salt, and 150 parts by weight of a neotrehalose syrup prepared by concentrating a solution containing about 66 w/w % of neotrehalose which had been prepared by the method and purification in Example A1-2 to give a concentration of about 70 w/w %, were mixed to homogeneity, admixed with 280 parts by weight of eggs, and gradually added to 1,000 parts by weight of boiling milk. The mixture was heated while stirring, and the heating was stopped when the whole mixture became semi-transparent. The resultant mixture was cooled, and vanilla flavor added. The mixture was weighed, filled up and packaged to obtain the captioned product.

The product has a smooch gloss, moderate sweetness and satisfactory taste. The product can be advantageously used as a COMPOSITION.

EXAMPLE B4

"Uiro-no-moto" (premix of sweet rice jelly)

An uiro-no-moto was prepared by mixing to homogeneity 90 parts by weight of rice powder, 20 parts by weight of corn starch, 120 parts by weight of a crystalline neotrehalose powder obtained by the method in Example A2, and 4 parts by weight of pullulan. The mixture was kneaded with adequate amounts of "matcha" (powdered green tea) and water, and the resultant mixture was placed in a vessel and steamed up over a period of 60 minutes to obtain an uiro containing matcha.

The product has a satisfactory gloss, biting-property and flavor. The shelf-life of the product is relatively long because the retrogradation of starch in the product is inhibited. The product can be advantageously used as COMPOSITION.

EXAMPLE B5

Lactic acid beverage

Ten parts by weight of defatted milk was sterilized by heating at 80° C. for 20 minutes, cooled to 40° C., 0.3 parts by weight of a starter was added, and the mixture was fermented at about 37° C. for 10 hours. Thereafter, the mixture was homogenized and added to 4 parts by weight of a crystalline neotrehalose powder obtained by the method in Example A2, one part by weight of sucrose, and 2 parts by weight of an isomerized syrup. The resultant mixture was sterilized at 70° C., cooled, a flavoring agent was added, and the mixture was bottled to obtain the captioned product.

The product is a high-quality lactic acid beverage having a sour taste which has a satisfactory blend of flavor and sweetness. The product can be advantageously used as a COMPOSITION.

EXAMPLE B6

Fruit-juice powder

Thirty-three parts by weight of pulverized orange juice prepared by spray-drying was stirred and mixed to homogeneity with 50 parts by weight of a crystalline neotrehalose specimen obtained by the method in Example A1-2, 10 parts by weight of sucrose, 0.65 parts by weight of anhydrous citric acid, 0.1 part by weight malic acid, 0.1 part by weight of L-ascorbic acid, 0.1 part by weight of sodium citrate, 0.5 parts by weight of pullulan, and a powdery flavoring agent. The mixture was pulverized, and the resultant powder was fed to a fluidized-bed granulator and granulated at an inlet temperature of 40° C. and an air-flow-rate of 150 m$^3$/min for 30 minutes while spraying the content with a high-neotrehalose content solution, obtained by the method in Example A2, as a binder. Thereafter, the resultant was weighed and packaged to obtain the captioned product.

The product is a fruit-juice powder having an orange juice content of about 30 w/w %. The product is free of any disagreeable taste and odor, and is stable over a relatively-long time period without absorbing moisture and thereby solidifying. The product can be advantageously used as a COMPOSITION.

EXAMPLE B7

Solid intubation-nutrient

A composition was prepared by mixing 500 parts by weight of a crystalline neotrehalose specimen obtained by the method in Example A1-2, 270 parts by weight of dried egg yolk, 209 parts by weight of defatted milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate, and 0.04 part by weight of nicotinamide. Twenty-five g aliquots of the composition were distributed into laminated-aluminum small bags, and the bags were heat sealed to obtain the captioned product.

In use, one bag of the product is first dissolved in an about 150–300 ml water to prepare an intubation nutrient solution, which is then orally administered or administered through intubation feeding, for example, into nasal cavity, gullet and stomach. The product can be advantageously used as a COMPOSITION.

EXAMPLE B8

Infusion solution

A crystalline neotrehalose specimen prepared by the method in Example A1-2 was dissolved in water to give a concentration of about 10 w/v %, and the solution was subjected, in a conventional manner, to membrane filtration, aseptically distributed into a plastic bottle, and sealed to obtain the captioned product.

The product is a stable agent free of change on standing and can be favorably used in intravenous- and intraperitoneal-injections which supplement energy to a living body. The product is isotonic at a concentration of 10 w/v % to the blood and supplies energy to a living body at 2-fold higher concentration than in the case of glucose.

EXAMPLE B9

Infusion solution

A crystalline neotrehalose specimen was dissolved in water to give a concentration of 20 w/v %, and the solution was subjected, in a conventional manner, to membrane filtration, aseptically distributed into a plastic bag and sealed to obtain the captioned product.

The product is stable and free of change on standing and can be favorably admixed with other medicaments and/or COMPOSITIONs and adjusted to an appropriate concentration, prior to administration.

EXAMPLE B10

Infusion solution

A crystalline neotrehalose and a crystalline sorbitol were mixed and dissolved in water to give concentrations of 5 w/v % and 2.5 w/v % respectively, and the mixture was distributed, similarly as in Example B8, into a bottle and sealed to obtain the captioned product.

The product is stable and free of change on standing and can be favorably used in intravenous- and intraperitoneal-injections which supply amino acids and energy to a living body.

EXAMPLE B11

Infusion solution

A crystalline neotrehalose specimen prepared by the method in Example A1-2 and an amino acid composition having the following components were dissolved in water to give concentrations of 5 w/v % and 3.0 w/v % respectively, and the mixture was purified, similarly as in Example B8, distributed into a bag and sealed to obtain the captioned product.

| Components of amino acid composition | mg/100 ml |
| --- | --- |
| L-Isoleucine | 180 |
| L-Leucine | 410 |
| L-Lysine hydrochloride | 620 |
| L-Methionine | 240 |
| L-Phenylalanine | 290 |
| L-Threonine | 180 |
| L-Tryptophan | 60 |
| L-Valine | 200 |
| L-Arginine hydrochloride | 270 |
| L-Histidine hydrochloride | 130 |
| L-Glycine | 340 |

Although the product is a complex agent which contains saccharide and amino acids, it is stable and free of change on standing because of the non-reducibility of neotrehalose, and can be favorably used in intravenous- and intraperitoneal-injections. The product is suitably used as COMPOSITION to supply both energy and amino acids to a living body.

EXAMPLE B12

Infusion solution

One hundred parts by weight of a 10 w/v % aqueous neotrehalose solution was added with 5 parts by weight of soybean and 1.5 parts by weight of lecithin from egg yolk, and the mixture was subjected to a mixer to obtain a partial homogenate which was then mixed to homogeneity with a device commercialized by Gaulin Co., U.S.A., under nitrogen atmosphere and at a pressure of 600 kg/cm² into minute droplets of O/W emulsion, average particle size of 0.2 μm or lower. Similarly as in Example B9, the emulsion was distributed into a bag and sealed to obtain the captioned product.

Although the product is a complex COMPOSITION which contains a saccharide and lipids, it is stable and free of change on standing and can be favorably used as a composition for intravenous- and intraperitoneal-injections.

EXAMPLE B13

Infusion solution

An aqueous solution containing as minerals 0.136 w/v % sodium dihydrogenphosphate, 0.098 w/v % potassium acetate, 0.031 w/v % magnesium chloride hexahydrate, 0.022 w/v % calcium chloride dihydrate, 1.59 w/v % sodium lactate was prepared by adding and dissolving the minerals in a 10 w/v % aqueous neotrehalose solution. The aqueous solution was adjusted to pH 5.5, and distributed, similarly as in Example B9, and sealed to obtain the captioned product.

The product is stable and free of change on standing and can be favorably used as a composition for intravenous- and intraperitoneal-injections which supply energy and minerals to a living body.

EXAMPLE B14

Infusion solution

An aqueous solution containing 0.1 w/v % human serum albumin and 100,000 international units per ml of human interferon-α was prepared by dissolving human serum albumin and human interferon-α in a 20 w/v % aqueous neotrehalose solution. The aqueous solution was subjected to membrane filtration, aseptically distributed into a 10ml-bottle and sealed to obtain the captioned product.

The neotrehalose in the product stabilizes the human interferon-α as a biologically active substance, and this renders the human interferon-α stable for a relatively-long time period when stored under light-shielded conditions. The product can be advantageously used to attain a therapeutic effect exerted by the biologically active substance, as well as to supply energy to a living body by dissolving the product in distilled water for injection or by using the product with another COMPOSITION in combination, prior to use.

EXAMPLE B15

Traumatic in the form of ointment

Five hundred parts by weight of a crystalline neotrehalose specimen, prepared by the method in Example A2, was admixed with 50 parts by weight of a methanol solution which had been prepared by dissolving 3 parts by weight of iodine in methanol, and the resultant mixture was admixed with 200 parts by weight of a 10 w/w % aqueous pullulan solution to obtain the captioned product having an appropriate spreadability and adhesiveness.

The product exerts an antibacterial action inherent to iodine and acts as a COMPOSITION via the action of neotrehalose, and these shorten the healing time period and cure the affected part to look as beautiful as before.

EXAMPLE B16

Sugar-coated tablet

A plain tablet (150 mg in weight) as a core tablet was coated with the first sugar-coating composition consisting of 40 parts by weight of a crystalline neotrehalose specimen obtained by the method in Example A1-2, 2 parts by weight of pullulan (average molecular weight of 200,000), 30 parts by weight of water, 25 parts by weight of talc, and 3 parts by weight of titanium oxide until the tablet weighed about 230 mg. Thereafter, the resultant tablet was first coated with the second sugar-coating composition consisting of 65 parts by weight of the same crystalline neotrehalose specimen as used in the above, one part by weight of pullulan (average molecular weight of 200,000) and 34 parts by weight of water, then coated with a wax solution to impart a gloss. Thus, the captioned product having a gloss and satisfiable appearance was obtained.

The handleability in the sugar-coating step for the product is satisfactory, and the product has a satisfactory shock-resistance and maintains its quality at a relatively high-level over a relatively-long time period. The product can be advantageously used as a COMPOSITION.

[Effect of the invention]

As evident from above, the present SACCHARIDE which comprises neotrehalose is a stable and non-reducing saccharide, and, entirely different from trehalose ($\alpha,\alpha$-trehalose) and isotrehalose ($\beta,\beta$-trehalose) which are similar to neotrehalose. The present SACCHARIDE is readily metabolized and utilized in vivo.

The present COMPOSITION containing neotrehalose as effective ingredient dose not exhibit reducing properties and has a relatively-high storage stability. Thus, the present COMPOSITION is readily formulated into a favorable synthetic-nutritional-composition and a pharmaceutical composition with a higher therapeutic-effect by combining the present COMPOSITION with other nutritionally or therapuetically effective-substances.

While there has been described what is at present considered to be the preferred embodiments of the invention, it will be understood that various modifications may be made therein, and it is intended to cover in the appended claims all such modifications as fall within the true spirit and scope of the invention.

We claim:

1. A pharmaceutical composition which is comprised of a saccharide composition which contains at least 10% neotrehalose by weight and a pharmaceutically effective parenteral carrier and is characterized by:
   (a) being readily metabolized and utilized in a normal mammal;
   (b) being able to slightly increase the blood sugar level of said normal mammal but does not substantially increase the insulin level in said normal mammal when said composition is administered parenterally; and
   (c) being pharmaceutically more stable than a corresponding composition lacking neotrehalose.

2. The composition of claim 1, which is in the form of an infusion solution.

3. A process for preparing the pharmaceutical composition of claim 1 which comprises dissolving a saccharide composition and an amount of neotrehalose which results in a pharmaceutical composition that is 10% neotrehalose by weight in a pharmaceutically effective parenteral carrier.

4. A method for supplementing energy to mammals including humans while slightly increasing the blood sugar level of a normal mammal but not substantially increasing the insulin level in said normal mammal when administered with a saccharide composition which contains at least 10% neotrehalose by weight and a pharmaceutically effective parenteral carrier, said method consisting essentially of administering said composition to said mammals via parenteral route at a does or about 1 to 1000 g/day/adult of neotrehalose by weight.

5. The method of claim 4 wherein the dose of said composition is in the range of about 1–500 g/day/adult of neotrehalose by weight.

6. The method of claim 5 wherein said composition is in the form of an infusion solution.

7. The process of claim 4, wherein said neotrehalose is crystalline neotrehalose.

8. The process of claim 4, wherein said pharmaceutical composition has about 1–40 w/v % of neotrehalose.

9. The process of claim 4, wherein the dose of said composition is in the range of about 1–500 g/day/adult based on the dry weight of neotrehalose, d.s.b.

10. The method of claim 4, wherein said neotrehalose is in the form of a syrup or powder.

11. The method of claim 4, wherein said neotrehalose is crystalline neotrehalose.

12. The method of claim 4, wherein said neotrehalose is in the form of composition comprising at least 10 w/w % of neotrehalose, on a dry solid basis.

13. The method of claim 12, wherein said composition is an infusion solution.

* * * * *